US00PP16421P3

(12) United States Plant Patent

Brown, Jr.

(10) Patent No.: US PP16,421 P3
(45) Date of Patent: Apr. 4, 2006

(54) *PERSICARIA* PLANT NAMED 'SILVER DRAGON'

(50) Latin Name: ***Persicaria* sp.**
Varietal Denomination: Silver Dragon

(75) Inventor: Kenneth E. Brown, Jr., Tigard, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 133 days.

(21) Appl. No.: 10/884,489

(22) Filed: Jul. 1, 2004

(65) Prior Publication Data

US 2006/0005290 P1 Jan. 5, 2006

(51) Int. Cl.
*A01H 5/00* (2006.01)

(52) U.S. Cl. ..... Plt./263
(58) Field of Classification Search ..... None
See application file for complete search history.

(56) References Cited

U.S. PATENT DOCUMENTS

PP9,682 P * 11/1996 Bloom ..... Plt./263
PP12,062 P2 * 8/2001 Speichert ..... Plt./263

OTHER PUBLICATIONS http://www.cnb.nl/greenteam/newplants/english/cultivars/np266.htm.*

UPOV ROM GTITM Computer Database, GTI Jouve Retrieval Software 2005/02 Citation for 'Silver Dragon'.*

* cited by examiner

*Primary Examiner*—Anne Marie Grunberg
*Assistant Examiner*—W. C. Haas
(74) *Attorney, Agent, or Firm*—Klarquist Sparkman, LLP

(57) ABSTRACT

A new and distinct cultivar of *Persicaria* plant characterized by multicolored leaves exhibiting striking silver markings with olive green to brown edges and red purple stems and veins.

1 Drawing Sheet

Botanical classification: *Persicaria* sp.
Variety denomination: 'Silver Dragon'.

BACKGROUND OF THE INVENTION

The present invention relates to a new and distinct cultivar of an herbaceous perennial of the genus, *Persicaria,* and known by the cultivar name of 'Silver Dragon'. The genus *Persicaria* is a member of the family Polygonaceae.

The new cultivar is an open-pollinated seedling of *Persicaria microcephala* 'Red Dragon' (U.S. Plant Pat. No. 12,062). It was found in a cultivated area as a single plant growing among thousands of seedlings in a neighborhood backyard.

SUMMARY OF THE INVENTION

This new cultivar is characterized by:

1) Foliage with striking silver markings and colors.

2) Spreading habit.

The new variety has been reproduced only by asexual propagation (cutting and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
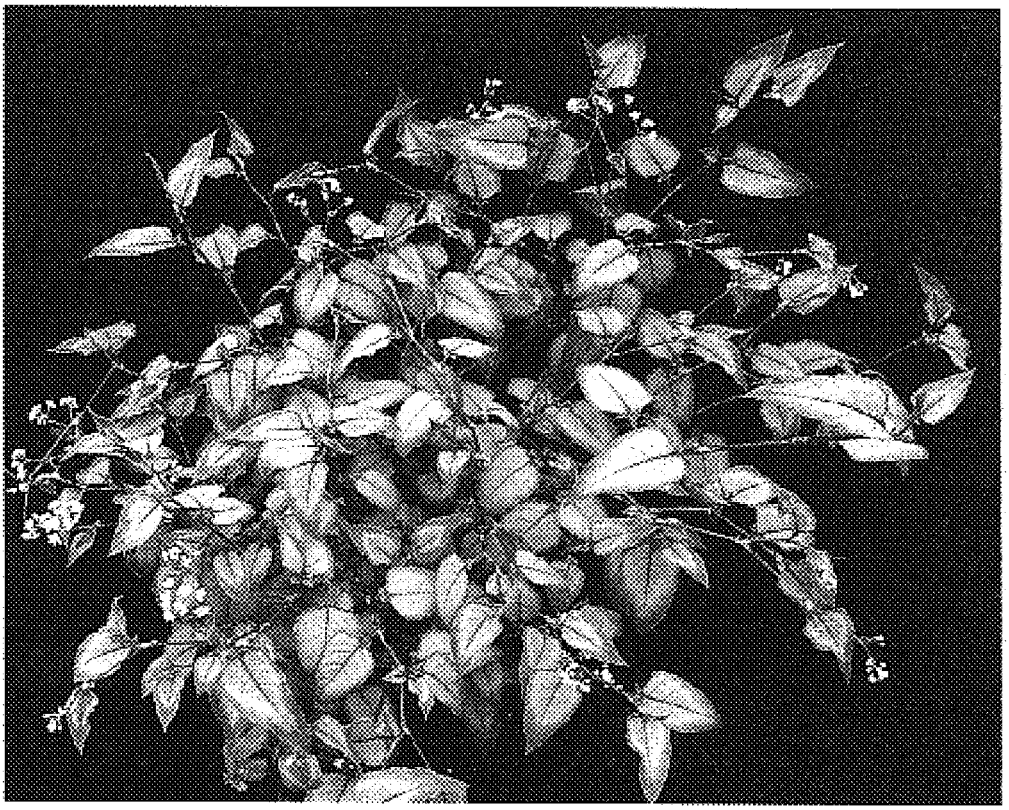
FIG. 1 shows a one-year-old greenhouse grown *Persicaria* 'Silver Dragon' growing in a container in Canby, Oreg.
Figure 2:
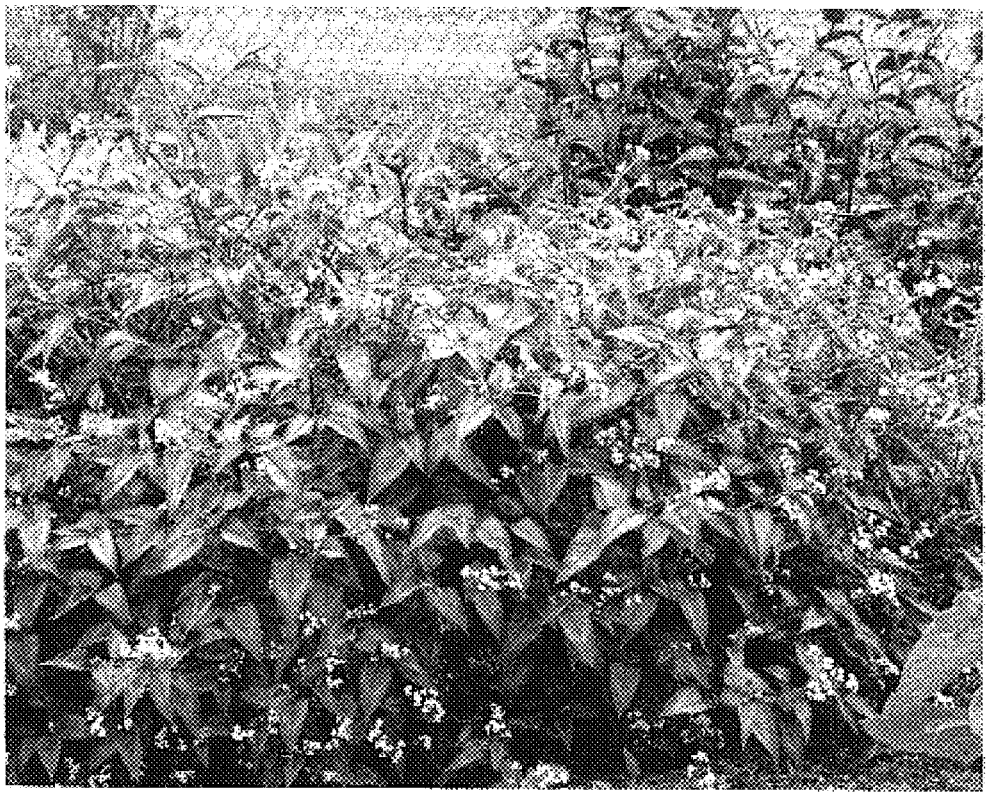
FIG. 2 shows a two-year-old plant growing in the ground in the garden in Canby, Oreg.

The following is a detailed description of the new cultivar based on observations of two-year-old specimens grown in the trial garden in Canby, Oreg. The color descriptions are all based on The Royal Horticultural Society Colour Chart.

Botanical name: *Persicaria* sp.
Cultivar name: 'Silver Dragon'.
Plant:
- *Form.*—Low, flat-topped mound.
- *Hardiness.*—USDA Zones 5 to 9.
- *Size.*—90 cm tall and 110 cm wide.
- *Habit.*—Clumping.

Stem:
- *Type.*—Succulent, with swollen nodes and sheath-like membranous stipules.
- *Size.*—4 mm diameter above the third node down from the tip, 1 cm diameter at plant base.
- *Surface.*—Glabrous.
- *Color.*—Dark red. Greyed Purple 183A.

Leaf:
- *Type.*—Simple.
- *Arrangement.*—Alternate.
- *Shape.*—Ovate.
- *Venation.*—Pinnate.

*Margins.*—Minutely denticulate and slightly undulate.
*Apex.*—Accuminate to cuspidate.
*Base.*—Attenuate with two basal lobes.
*Size.*—6 cm to 9.5 cm long and 3 cm to 4.4 cm wide.
*Vestiture.*—Sparsely pubescent.
*Aspect.*—Matte.
*Texture.*—Papery.
*Petiole length.*—0.5 cm to 1.3 cm and clasping at base.
*Petiole and major vein color.*—Greyed Purple 183A on top side to Greyed Red 178A on bottom side.
*Leaf color.*—Variable depending on the light intensity. Shade — Mature leaves topside: Overall mature leaves are green edged (Yellow Green 147A) with a large silver blotch toward the base (Greyed Green 191B) and dark purple along main vein and pooled at the leaf base before the lobes (Greyed Purple 187A). Basal lobes are Yellow Green 147A. Mature leaves bottom side: Closest to 148B except grayer and with a reddish cast around veins (Greyed Purple 184A). New leaves topside: Olive edged (closest to Brown 200C and slightly greener near tip, Yellow Green 147A) with a silver green band (Yellow Green 148C) in an inverted V pattern surrounding a brownish red blotch (closest to Brown 200D). Small basal lobes are also olive like the leaf edge. The leaf base near the vein is dark brown, Brown 200A. New leaves bottom side: Greyed Green 197A with a reddish cast along veins, Greyed Orange 176B. Sun — Mature leaves topside: Brown edged (Brown 200B) with a large silver blotch (Greyed Green 192C) and dark purple veins (Greyed Purple 187A). Late summer leaves fade to an olive green edge (Yellow Green 147A) with a silver V marking (Greyed Green 191B) and an olive triangular basal blotch (Greyed Green 189A) with purple veins (Red Purple 61A). Mature leaves bottom side: Looks red purple. Silver, Greyed Green 195A, suffused with pink, Greyed Purple 183C. New leaves topside: Brown edged (Brown 200B) with the pink blotch (Greyed Purple 183D) with a silver edge (Greyed Orange 177D). New leaves bottom side: Edges are Greyed Brown 189A and the rest is pink, Greyed Purple 185C.

Inflorescence:
*Type.*—Terminal compound corymbs.
*Number of flowers.*—41 per corymb.
*Corymb size.*—Variable. 5 cm wide and 4 cm deep without peduncle.
*Peduncle.*—Length — 1.5 cm to 2.5 cm. Diameter — 1.5 mm. Texture — Glabrous. Color — Yellow Green 152A.
*Pedicel.*—Texture — Glandular. Color — Yellow Green 146A.
*Bloom period.*—August to frost in Canby, Oreg.

Flower bud:
*Size.*—3 mm deep and 2 mm wide.
*Description.*—Ovoid.
*Color.*—White 155B with Yellow Green 145B at base.

Flower:
*Type.*—Perfect, actinomorphic.
*Shape.*—Campanulate.
*Size.*—2 mm deep and 2 mm wide.
*Petal lobes.*—5, overlapping.
*Petal color.*—White 155D with Yellow Green 145B at base.
*Petal texture.*—Waxy, thick.
*Calyx.*—Scarious and insignificant.
*Calyx color.*—Yellow Green 145B.
*Stamen number.*—8.
*Filaments.*—White 155D.
*Anther color.*—White 155D.
*Pollen color.*—White 155D.
*Pistil color.*—White 155D.
*Pistil.*—Three branched style, 3 capitulate stigmas.
*Fragrance.*—None.
*Lastingness.*—Each corymb blooms for about 3 weeks on the plant.

Fruit: Never seen.

Seed: Never seen. The plant is probably sterile.

Disease and pest resistance and tolerance: *Persicaria* as a genus are susceptible to aphids, slugs and snails. No insect or diseases have been noted on *Persicaria* 'Silver Dragon'.

COMPARISON TO *PERSICARIA* 'RED DRAGON'

Compared to its parent *Persicaria* 'Red Dragon', *Persicaria* 'Silver Dragon' is shorter and more branched with smaller and very different colored leaves, more silver than red. Both have red purple stems.

I claim:

1. A new and distinct hybrid of *Persicaria* plant substantially as shown and described, characterized by multicolored leaves exhibiting striking silver markings with olive green to brown edges and red purple stems and veins.

* * * * *